United States Patent
Klinder et al.

(10) Patent No.: US 10,219,773 B2
(45) Date of Patent: Mar. 5, 2019

(54) CHRONIC OBSTRUCTIVE PULMONARY DISEASE (COPD) PHANTOM FOR COMPUTED TOMOGRAPHY (CT) AND METHODS OF USING THE SAME

(71) Applicant: KONINKLIJKE PHILIPS N.V., Eindhoven (NL)

(72) Inventors: Tobias Klinder, Uelzen (DE); Rafael Wiemker, Kisdorf (DE); Udo Van Stevendaal, Ahrensburg (DE); Holger Schmitt, Luetjensee (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 926 days.

(21) Appl. No.: 14/418,471

(22) PCT Filed: Jul. 29, 2013

(86) PCT No.: PCT/IB2013/056204
§ 371 (c)(1),
(2) Date: Jan. 30, 2015

(87) PCT Pub. No.: WO2014/024087
PCT Pub. Date: Feb. 13, 2014

(65) Prior Publication Data
US 2015/0182185 A1    Jul. 2, 2015

Related U.S. Application Data
(60) Provisional application No. 61/680,735, filed on Aug. 8, 2012.

(51) Int. Cl.
*A61B 6/03* (2006.01)
*A61B 5/08* (2006.01)
(Continued)

(52) U.S. Cl.
CPC .............. *A61B 6/583* (2013.01); *A61B 5/085* (2013.01); *A61B 6/032* (2013.01); *A61B 6/0407* (2013.01);
(Continued)

(58) Field of Classification Search
None
See application file for complete search history.

(56) References Cited

U.S. PATENT DOCUMENTS 6,466,640 B1   10/2002   Taguchi
7,646,904 B2   1/2010    Summers et al.
(Continued)

FOREIGN PATENT DOCUMENTS

| JP | 2004245623 A | 9/2004 |
|---|---|---|
| KR | 2010059488 A | 6/2010 |
| WO | 2009081317 A1 | 7/2009 |

OTHER PUBLICATIONS

"Kim et al.," Semi-Automatic Measurement of the Airway Dimension by Computer Tomography Using the Full-Width-Half-Maximum Method: a Study of the Measurement Accuracy according to the CT Parameters and Size of the Airway Korean J Radiol. 9:-226-235 2008.*
(Continued)

*Primary Examiner* — Patricia J Park (57) ABSTRACT

An imaging system (10) analyzes airways of a patient. The system (10) includes a hardware phantom (50) including tubes (54) representative of airways. The tubes (54) include different lumen sizes and/or wall thicknesses. The system further includes an imaging scanner (12) for scanning a region of interest (ROI), including the airways, and the hardware phantom (50) to create raw image data. At least one processor (32) is programmed to at least one of: (1) correct measurements of walls of the airways based on measurements of lumen size and/or wall thickness of the
(Continued)

tubes (54) and known lumen size and/or wall thickness of the tubes (54); and (2) generate an image of the ROI in which color and/or opacity of the airways are based on a comparison of images or maps of the tubes (54) and images or maps of the airways. A corresponding method is also provided.

19 Claims, 4 Drawing Sheets

(51) Int. Cl.
    *A61B 6/00*     (2006.01)
    *A61B 6/04*     (2006.01)
    *A61B 5/085*     (2006.01)

(52) U.S. Cl.
    CPC .............. *A61B 6/463* (2013.01); *A61B 6/469* (2013.01); *A61B 6/50* (2013.01); *A61B 6/5205* (2013.01); *A61B 6/5217* (2013.01); *A61B 6/5235* (2013.01); *A61B 6/467* (2013.01)

(56) References Cited

U.S. PATENT DOCUMENTS

| | | |
|---|---|---|
| 9,060,676 B2 | 6/2015 | Blackhurst |
| 9,398,889 B2 * | 7/2016 | Kirby .................... A61B 6/032 |
| 2005/0201606 A1 | 9/2005 | Okada et al. |
| 2010/0278409 A1 * | 11/2010 | Wiemker ............... A61B 6/583 382/131 |
| 2011/0123083 A1 * | 5/2011 | Ojha ...................... G01N 24/08 382/131 |

OTHER PUBLICATIONS

Conradi, S. H., et al.; Measuring Small Airways in Transverse CT Images: Correction for Partial Volume Averaging and Airway Tilt; 2010; Acad. Radiol.; 17:1525-1534.

Kitsaka, T., et al.; Bronchial region extraction from 3D chest CT image by voxel classification based on local intensity structure; 2010; Third Int'l Workshop on Pulmonary Image Analysis; pp. 21-29.

Leader, J. K., et al.; Quantification of airway morphometry: the effect of CT acquisition and reconstruction parameters; 2007; Proc. of SPIE; 6511:65111R1-R7.

Robinson, T. E., et al.; An Airway Phantom to Standardize CT Acquisition in Multicenter Clinical Trials; 2009; Acad Radiol; 16:1134-1141.

Wiemker, R., et al.; Comparison of correction methods for bronchial lumen and wall thickness measurement using a physical tube array phantom; 2013; Proc. of SPIE; 8668:86684W1-W8.

* cited by examiner

CHRONIC OBSTRUCTIVE PULMONARY DISEASE (COPD) PHANTOM FOR COMPUTED TOMOGRAPHY (CT) AND METHODS OF USING THE SAME

CROSS REFERENCE TO RELATED APPLICATIONS

This application is a national tiling of PCT application Serial No. PCT/IB2013/056203, filed Jul. 29, 2013, published as WO 2014/024087 A1 on Feb. 13, 2014, which claims the benefit of U.S. provisional application Ser. No. 61/680,735 filed Aug. 8, 2012, which is incorporated herein by reference.

The present application relates generally to medical imaging. It finds particular application in conjunction with chronic obstructive pulmonary disease (COPD) diagnosis based on computed tomography (CT) and will be described with particular reference thereto. However, it is to be understood that it also finds application in other usage scenarios and is not necessarily limited to the aforementioned application.

COPD is an umbrella term used to describe chronic lung diseases that cause limitations in lung airflow. The main subtypes of COPD include emphysematic and bronchial COPD. According to the World Health Organization, COPD is one of the main causes of death worldwide. Further, the incidence rate of COPD is expected to increase, particularly in developing nations.

To diagnose COPD, airway wall thickness measurements from diagnostic CT are of main interest. Such measurements can provide early indications, or indications of the severity, of the disease. One approach for measuring airway wall thickness is the so-called parametric approach. The parametric approach includes lung segmentation, airway segmentation, airway tree labeling, segmentation of inner and outer airway walls, measurement at automatically selected locations in the airway tree, and reporting numerical results.

Figure 1:
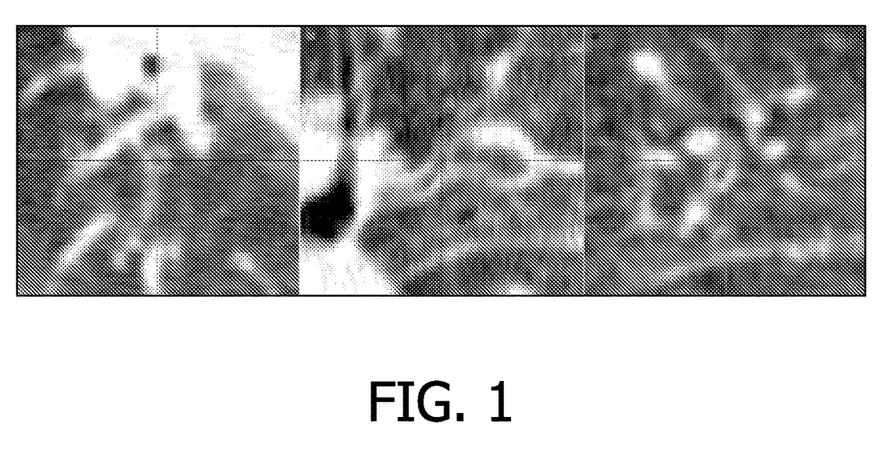
FIG. 1 illustrates portions of a computed tomograph (CT) image of a lung.

Accurately measuring airway wall thickness can be challenging. In many cases, the appearance of the airway wall in a CT image is heavily affected by partial volume effects and blur. Referring to FIG. 1, portions of a CT image of a lung are illustrated. As can be seen, limited physical resolution (i.e., blur), as well as partial volume effect (of voxel grid), heavily impact the ability to reliably measure the wall thickness of airways.

One approach to limit the partial volume effect and estimate the airway wall with sub-voxel accuracy is to estimate the scanner parameters for a specific scan. The images generated by CT are heavily affected by a variety of scanner parameters (e.g., reconstruction type, reconstruction resolution, tube current, etc.). Hence, different measurements can be obtained depending on the scanner parameters.

The present application provides a new and improved system and method which overcome the above-referenced problems and others.

In accordance with one aspect, an imaging system analyzes airways of a patient. The system includes a hardware phantom including a plurality of tubes representative of airways. The plurality of tubes include different lumen sizes and/or wall thicknesses. The system further includes an imaging scanner for scanning a region of interest (ROI), including the airways, and the hardware phantom to create raw image data. At least one processor is programmed to at least one of: (1) correct measurements of walls of the airways based on measurements of lumen size and/or wall thickness of the plurality of tubes and known lumen size and/or wall thickness of the plurality of tubes, the measurements made from the raw image data; and (2) generate an image of the ROI in which color and/or opacity of the airways are based on a comparison of images or maps of the plurality of tubes and images or maps of the airways, the images or maps generated from the raw image data.

In accordance with another aspect, a method analyzes airways of a patient. The method includes receiving raw image data from an imaging scanner which scans a region of interest (ROI), including the airways, and a hardware phantom. The hardware phantom includes a plurality of tubes representative of airways, the plurality of tubes including different lumen sizes and/or wall thicknesses. The method further includes at least one of: (1) correcting measurements of walls of the airways based on measurements of lumen size and/or wall thickness of the plurality of tubes and known lumen size and/or wall thickness of the plurality of tubes, the measurements made from the raw image data; and (2) generating an image of the ROI in which color and/or opacity of the airways are based on a comparison of images or maps of the plurality of tubes and images or maps of the airways, the images or maps being generated from the raw image data.

In accordance with another aspect, a hardware phantom for diagnostic imaging is provided. The hardware phantom includes a plurality of tubes representative of typical airway sizes and arranged in a two-dimensional grid, wherein a lumen size of the plurality of tubes increases along one of the axis of the grid and wall thickness increases along the other axis of the grid.

One advantage resides in more accurate evaluation of breathing passages.

Another advantage resides in a two-dimensional projection image allowing visualization of the extent of airway wall thickening at a single glance.

Another advantage resides in easy navigation within a three-dimensional computed tomograph (CT) image based on the two-dimensional projection image.

Another advantage resides in parallel implementation.

Another advantage resides in calibration of CT scanner parameters.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
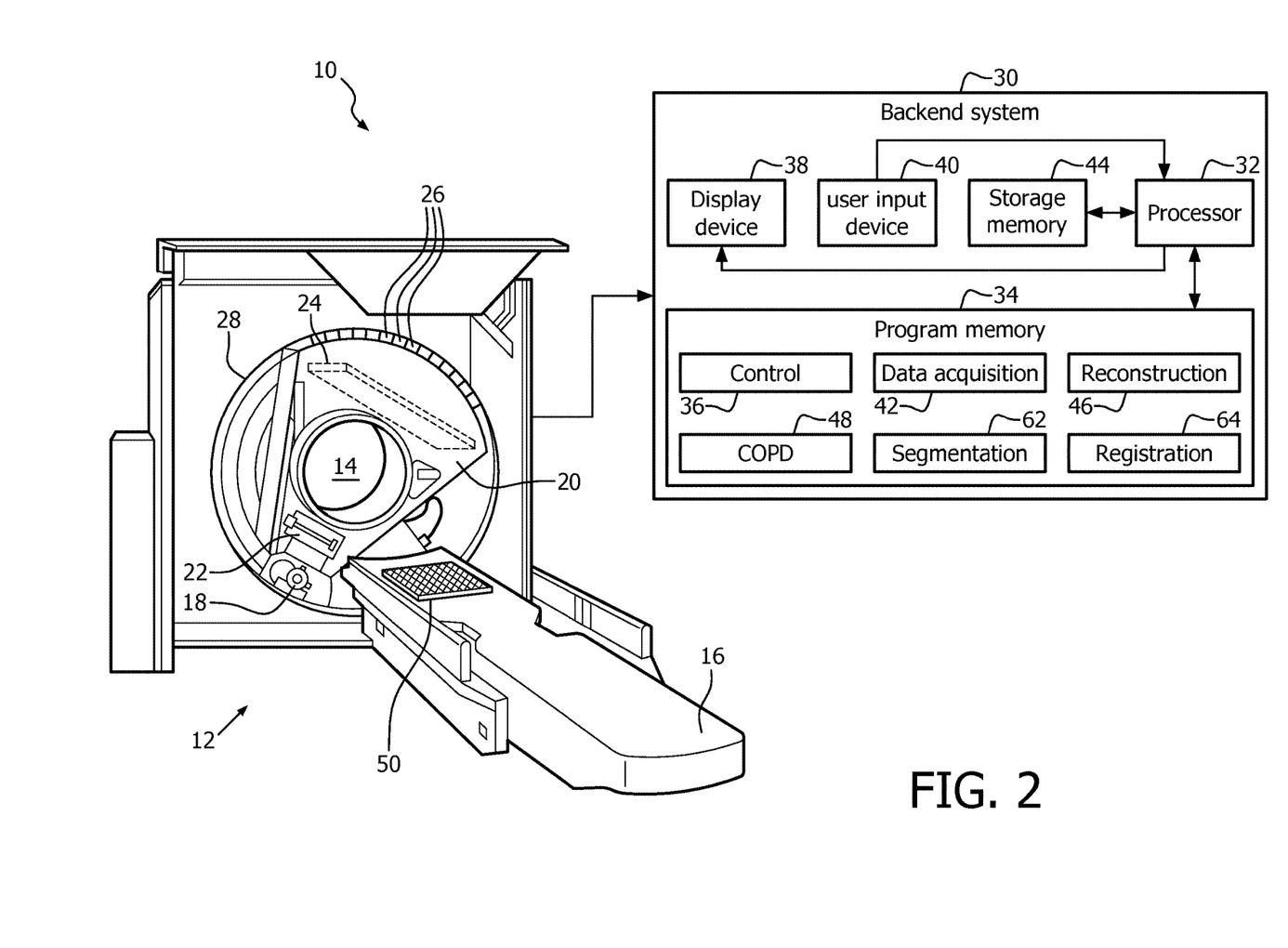
FIG. 2 illustrates a CT system.

With reference to FIG. 2, a computed tomograph (CT) system 10 utilizes CT to perform one or more diagnostic scans of a region of interest (ROI) of a patient, such as thoracic region of the patient. The CT system 10 includes a scanner 12 defining an examination volume 14. The examination volume 14 is sized to accommodate the patient, which is positioned in the examination volume 14 during a scan. A patient support 16 supports the patient in the scanner 12 and facilitates positioning the patient in the examination volume 14.

An x-ray tube assembly 18 mounted on a rotating gantry 20 projects one or more beams of radiation through the examination volume 14, and a collimator 22 collimates the beams of radiation in a beam thickness dimension. In third generation scanners, a two-dimensional x-ray detector 24 is disposed on the rotating gantry 20 across the examination volume 14 from the x-ray tube assembly 18. In fourth generation scanners, a ring or array of two-dimensional x-ray detectors 26 is mounted on a stationary gantry 28 surrounding the rotating gantry 20. The two-dimensional x-ray detectors 24, 26 generate data indicative of the integrated x-ray absorption along a corresponding beam between the x-ray tube assembly 18 and the two-dimensional x-ray detectors 24, 26.

Each of the two-dimensional x-ray detectors 24, 26 includes a two-dimensional array of photodetectors connected to, or preferably integrated into, an integrated circuit. The photodetectors directly or indirectly detect radiation (i.e., x-ray photons) from the x-ray tube assembly 18 and, based upon the detected radiation, generate the absorption data. Examples of the photodetectors include digital or analog silicon photomultipliers (SiPMs), photodiodes, and other opto-electric transducers.

If the photodetectors cannot directly detect the radiation, the two-dimensional x-ray detectors 24, 26 typically include one or more scintillators optically coupled to the photodetectors between the x-ray tube assembly 18 and the photodetectors. When an x-ray photon deposits energy in the scintillators, the scintillators scintillate and emit visible-light photons toward the photodetectors, which the photodetectors can directly detect. Examples of scintillators include scintillator plates, or individual scintillation or pixelated crystals, made from materials such as gadolinium oxysulfid (GOS), bismuth germanate (BGO), cesium iodide, yttrium silicate, sodium iodide (NaI), and the like.

A backend system 30 coordinates the diagnostic scans of the ROI. The backend system 30 is remote from the scanner 12, and includes at least one processor 32 and at least one program memory 34. The program memory 34 includes processor executable instructions that, when executed by the processor 32, coordinate the diagnostic scans. The processor 32 executes the processor executable instructions to coordinate the diagnostic scans.

A control module 36 of the processor executable instructions controls overall operation of the backend system 30. The control module 36 suitably displays a graphical user interface (GUI) to a user of the backend system 30 using a display device 38 of the backend system 30. Further, the control module 36 suitably allows the user to interact with the GUI using a user input device 40 of the backend system 30. For example, the user can interact with the GUI to instruct the backend system 30 to coordinate the diagnostic scans.

A data acquisition module 42 of the processor executable instructions performs scans, including the diagnostic scans, of the ROI. For each scan, the data acquisition module 42 controls the scanner 12 according to scanner parameters of the scan. While controlling the scanner 12, the data acquisition module 42 acquires the absorption data, as well as data on the angular position of the rotating gantry 20, which is typically stored in at least one storage memory 44 of the backend system 30 as a raw image data set.

A reconstruction module 46 of the processor executable instructions reconstructs the raw image data sets into images and/or maps of the ROI. Various known reconstruction techniques are contemplated including spiral and multi-slice scanning techniques, convolution and back projection techniques, cone beam reconstruction techniques, and the like. The images and/or maps are typically stored in the storage memory 44 and/or displayed on a display device, such as the display device 38.

Figure 3:
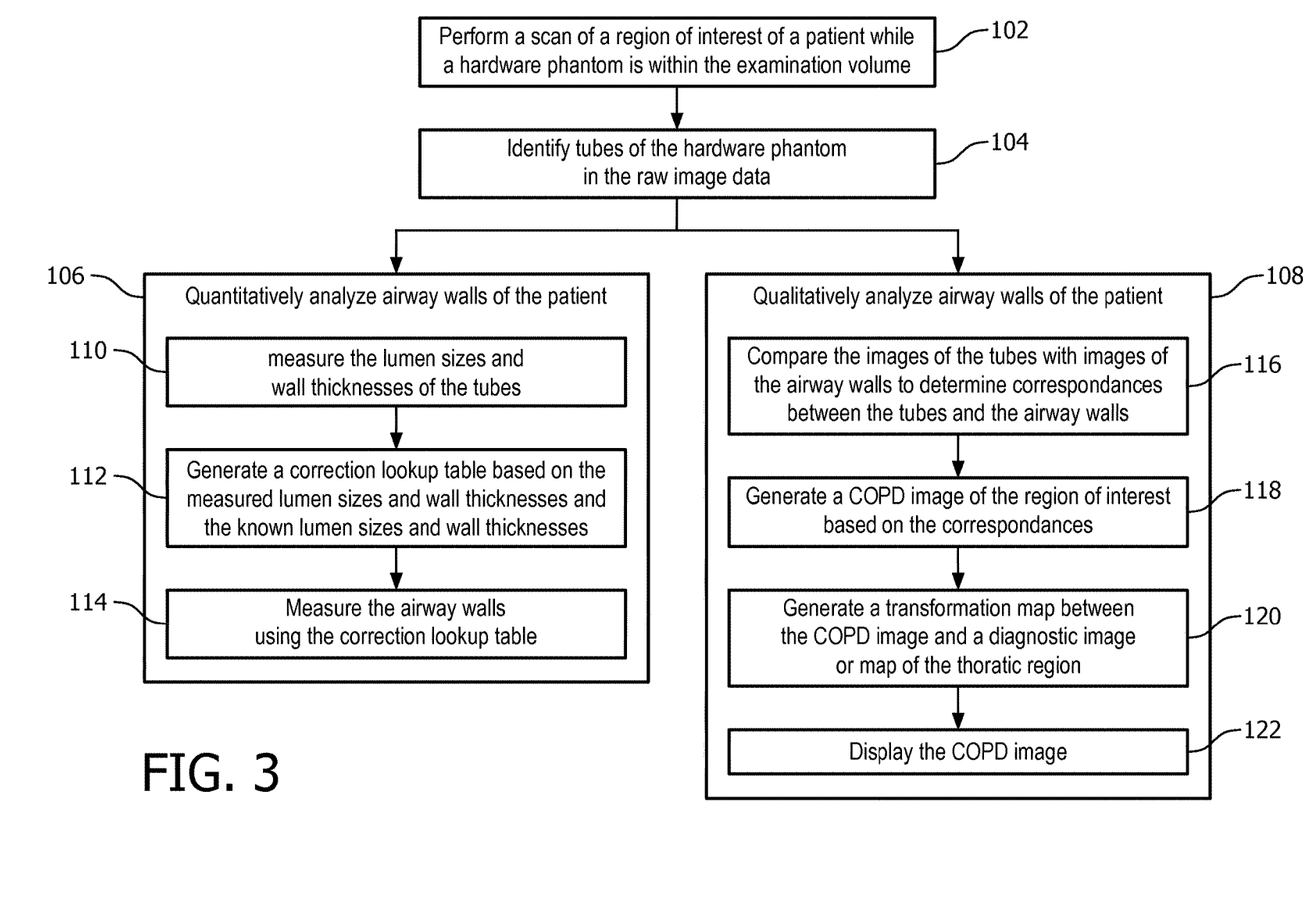
FIG. 3 illustrates a method of diagnosing chronic obstructive pulmonary disease (COPD).

A chronic obstructive pulmonary disease (COPD) module 48 of the processor executable instructions coordinates diagnosis of COPD according to the method 100 of FIG. 3. The method 100 includes performing 102 a scan of the ROI while one or more hardware phantoms 50 are positioned within the examination volume 14. The hardware phantoms 50 can be positioned at various locations within the examination volume 14, such as on the patient. However, placing the hardware phantoms 50 on the patient can introduce motion artifacts. Hence, the hardware phantoms 50 are preferably embedded within or mounted on the scanner 12 or the patient support 16. The scan is typically one of the diagnostic scans, but can be another scan (e.g., a calibration scan), and the scan is performed using the data acquisition module 42.

Figure 4:
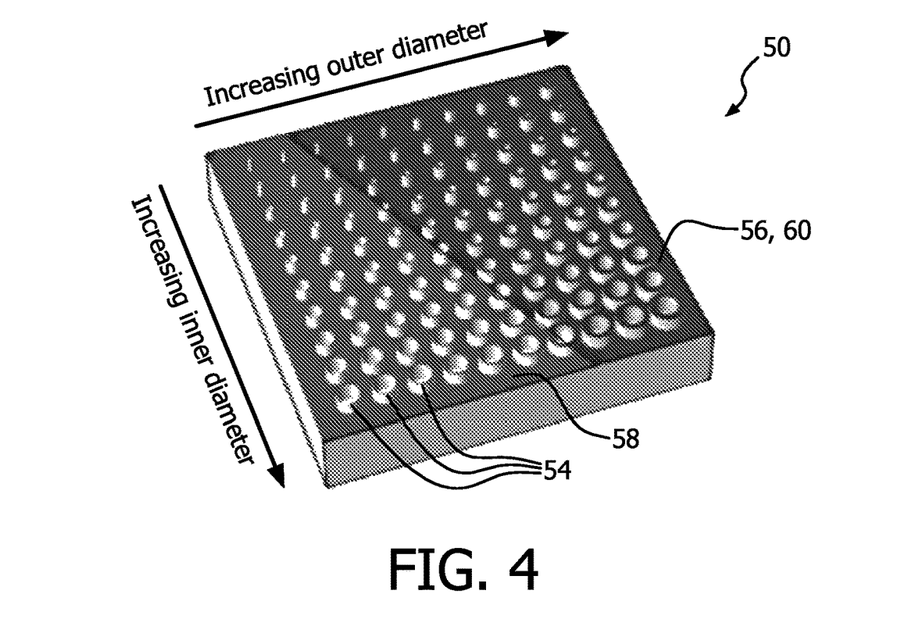
FIG. 4 illustrates a hardware phantom.

With further reference to FIG. 4, each of the hardware phantoms 50 includes an array of tubes 54 or an airway phantom built from real patient data. The array can be one-dimensional, two-dimensional, or three-dimensional, and includes a plurality of the tubes 54, for example, arranged in a grid. The tubes 54 are representative of typical and/or atypical airway walls, and include varying lumen size and wall thickness, which are known. Suitably, the tubes 54 include a tube for each combination of lumen size and wall thickness from the lumen sizes spanning from 1-10 millimeters (mms) in 1 mm increments and the wall thicknesses spanning from 0.1-5 mms in 0.1 mm (or 0.2 mm) increments. Further, the axes of the tubes 54 are advantageously parallel. Although illustrated in FIGS. 1 and 4 as extending perpendicular to the patient, the tubes 54 can have other orientations, such as parallel to a central axis of the patient. Also, sets of tubes extending in each of a plurality of directions are contemplated.

The tubes 54 are formed from a material (e.g., plastic) with Hounsfield unit (HU) values similar to airway walls, and embedded within a structure 56 formed from a material (e.g., plastic) with HU values similar to lung parenchyma. Further, the tubes 54 can also be physically and/or virtually color coded to distinguish between tubes representative of healthy airway walls and tubes representative malignant airway walls. The tubes 54 of the phantom 50 can be color or CT readably physically encoded and/or the portion of reconstructed image representing the phantom 50 can be color coded. For example, red can indicate malignancy, green can indicate healthy. A gradient in the color can be employed to indicate the extent of the health or malignancy. For example, the darker the green a tube is, the healthier the airway wall it represents is, and the darker the red a tube is, the more malignant the airway wall it represents is.

As illustrated in FIG. 4, one example of the hardware phantom 50 is provided. The hardware phantom 50 includes a two-dimensional array of the tubes 54. Along one axis of the array, the inner diameter of the tubes 54 remains fixed, while the outer diameter of the tubes 54 increases. In other words, the wall thickness increases. Along the other axis of the array, the inner diameter of the tubes 54 increases, while the outer diameter of the tubes 54 increases. In other words, the lumen size increases. The one embodiment, the lumen size spans from 1-10 mms in 1 mm increments, and the wall thickness spans from 2-4 mms in 0.2 mm increments. The array includes healthy airway walls shown in a first region 58, and malignant airway walls shown in a second region 60.

The hardware phantom 50 in the illustrated embodiment only includes a single array of parallel tubes. However, because the scanner 12 is typically not isotropic, it may be advantageous to employ a plurality of the hardware phantoms 50 with different orientations to axially align tubes along each axis of the scanner 12. For example, a two-dimensional hardware phantom can be oriented along each of the sagittal, coronal and transverse planes.

Figure 5:
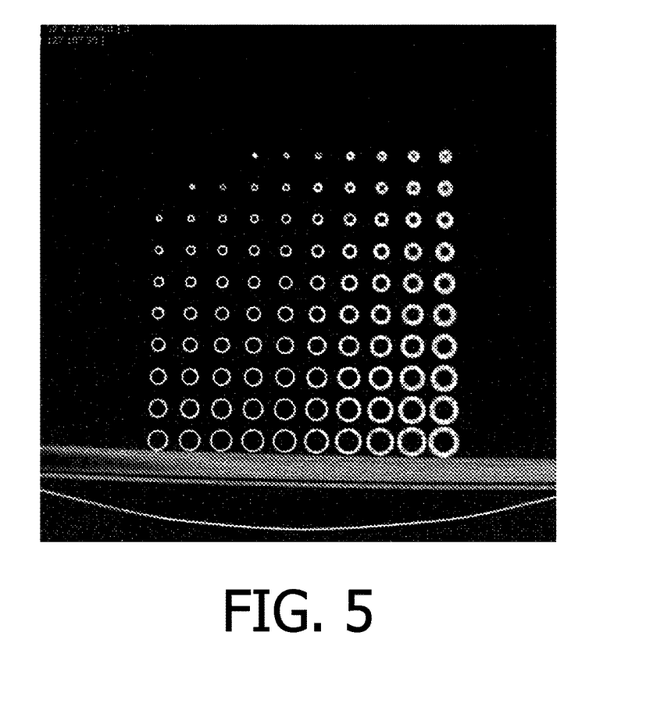
FIG. 5 illustrates a CT image of the hardware phantom of FIG. 4.

With reference again to FIG. 3, after performing the scan, the tubes 54 of the hardware phantoms 50 are identified 104 within the raw image data using a segmentation module 62 of the processor executable instructions. The identification 104 can be performed automatically and/or manually. As to automatic identification, a segmentation algorithm is employed, the segmentation algorithm being one of any number of known segmentation algorithms. Depending upon the segmentation algorithm, the reconstruction module 46 can be employed to convert the raw image data set to an image or map. The tubes 54 can be identified based on geometric location, physical dimensions, imagable markers, or the like. As to manual identification, the reconstruction module 46 is employed to convert the raw image data set to an image or map. The image or map is then displayed on the GUI and the user identifies the tubes 54 of the hardware phantoms 50 thereon. FIG. 5 illustrates an example image or map of the hardware phantom 50 of FIG. 4.

Having identified the tubes 54 of the hardware phantoms 50 within the raw image data set, the airway walls of the patient are quantitatively 106 and/or qualitatively 108 analyzed. When the scan is one of the diagnostic scans, the airway walls are typically extracted from the raw image data set of the scan. However, as noted above, the scan does not need to be one of the diagnostic scans. Hence, when the scan is not one of the diagnostic scans, the airway walls are typically extracted from the raw image data set of another scan, such as one of the diagnostic scans.

Quantitative analysis 106 includes measuring 110 the lumen sizes and wall thicknesses of the tubes 54 from the reconstructed three-dimensional CT image data set. A correction lookup table is the generated 112 correlating the physical phantom tube lumen sizes and wall thicknesses of the tubes 54 known from physical measurements of the phantom tubes 54 and lumen sizes and wall thicknesses measured in the 3D CT image data set. The correction lookup table includes an entry for each combination of measured lumen size and thickness. The entry for a combination of measured lumen size and thickness includes the measured lumen size and thickness, as well as a correction factor or the known lumen size and thickness. In another embodiment, a common correction factor or correction equation, curve, or algorithm is derived.

Using the correction lookup table, the airway walls are measured 114 within the raw image data set of the diagnostic scan. This includes initially measuring the airway walls of the patient using any of various well known techinques, but preferably the same technique that was used to measure the phantom tubes 54. For example, the airway tree of the patient is automatically extracted, and the airway walls are automatically extracted from the extracted airway tree. Lumen size and wall thickness are then measured from the extracted airway walls.

After determining the initial measurements, the initial measurements can be corrected using the correction lookup table by finding the corresponding entry. For example, correction factors or actual measured values can be looked up based on the initial measurements. Insofar as an exact entry is not found, interpolation or the like can be employed.

The corrected measurements, or only those corrected measurements which are atypical, can be displayed on a display device, such as the display device 38. The corrected measurements can also be linked to an image or map of the diagnostic scan so the user can visually review an airway wall on the display device by selecting the corresponding measurement using a user input device, such as the user input device 40. Color coding the diagnostic images can be utilized to identify potential disease affected airway tubes.

Qualitative analysis 108 includes comparing 116 the images or maps of the tubes 54 of the hardware phantoms 50 with images or maps of the airway walls of the patient to determine correspondances between the tubes 54 and the airway walls. The images or maps of the airway walls are typically determined from the raw image data set of the diagnostic scan, and the images or maps of the tubes 54 are determined from the raw image data set of the scan. As noted above, the scan and the diagnostic scan can be the same scan. Suitably, the reconstruction module 46 is employed to generate the images or maps.

One approach for performing the comparing 116 is through the use of radial intensity profiles. A radial intensity profile is computed in the image for each of the tubes 54 of the hardware phantom arrays 50. Further, a radial intensity profile is computed for each of the voxels (corresponding to airway tubes) of the ROI. For each airway tube, the radial intensity profile is matched against the radial intensity profiles of all the tubes 54 using a similarity measure. The tube with the best match score corresponds to the voxel.

After determine a correspondance, a COPD image of the ROI is generated 118. The COPD image can be two- or three-dimensional, but is typically two dimensional. For example, the COPD image can be a maximum intensity projection (MIP) or a direct volume rendering (DVR). Within the COPD image, the color and/or opacity of the voxels are adjusted based the colors assigned to the tubes 54 and the match scores. For example, the opacity of each voxel is based on the match score of the best matching tube, and/or the color of each voxel is the color code of the best matching tube. As to the former, locations with low match scores will essentially be transparent. Typically, opacity is only employed when the COPD image is two-dimensional. Further, when the COPD image is two-dimensional, the foreground priority is given by the degree of anomaly (i.e., degree of malignancy), so that anomalous locations are shown in the foreground. The degree of anomaly of a voxel can be determined from the degree of anomaly of the best matching tube.

As noted above, the tubes 54 can be physically and/or virtually color coded to distinguish between tubes representative of healthy airway walls and tubes representative malignant airway walls. For example, red can indicate malignancy, green can indicate healthy. A gradient in the color can be employed to indicate the extent of the health or malignancy. For example, the darker the green a tube is, the healthier the airway wall it represents is, and the darker the red a tube is, the more malignant the airway wall it represents is.

A transformation map between the COPD image and a diagnostic image or map generated 56 from the diagnostic scan is generated 120 using a registration module 64 of the processor executable instructions. The registration module 64 generates the transformation map using one of any number of well known registration algorithms. The COPD image is then displayed 122 on a display device, such as the display device 38. Selection of a pixel, voxel, or the like of the COPD image using a user input device, such as the user input device 40, displays the corresponding portion within the diagnostic image and/or the phantom image on the display device. The corresponding portion is determined using the transformation map. When the diagnostic image is two-dimensional, a pixel may correspond to multiple portions within the diagnostic image or map, such as when the diagnostic image or map is three-dimensional. In such a case, the corresponding portion is the portion which contributed with highest opacity along the view line of the pixel.

The foregoing approaches to qualitatively and/or quantitatively analyzing the airway walls of the patient are set forth by way of example. It is to be appreciated that other approaches based on the hardware phantoms 50 are contemplated. For example, images or maps of the tubes 54 of the hardware phantoms 50 can be displayed (e.g., using the display device 38) with images or maps of the airway walls of the patient so as to to allow visual comparison, such as in a side-by-side arrangement. In this example, selection (e.g., using the user input device 40) of a tube of the hardware phantom on the images or maps of the tubes 54 can highlight (e.g., using color coding) the corresponding airway wall(s) of the patient on the images or maps of the airway walls. Similarly, selection (e.g., using the user input device 40) of an airway wall of the patient on the images or maps of the airway walls can highlight the corresponding tube of the hardware phantom on the images or maps of the tubes 54. Further, it is also contemplated that scanner parameters can be adjusted or otherwise calibrated (e.g., for scale, distortion, or the like) through comparison of measured lumen sizes and wall thicknesses of the tubes 54 with known lumen sizes and wall thicknesses of the tubes 54.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system for analyzing airways of a patient, said system comprising:
a hardware phantom including a plurality of tubes representative of airways, the plurality of tubes including different lumen sizes and/or wall thicknesses;
an imaging scanner; and,
at least one processor programmed to:
control the imaging scanner to scan a region of interest (ROI), including the airways of the patient and the hardware phantom to create raw image data; and
at least one of:
correct measurements of walls of the airways based on measurements of lumen size and/or wall thickness of the plurality of tubes and known lumen size and/or wall thickness of the plurality of tubes, the measurements made from the raw image data; and,
generate an image of the ROI in which color and/or opacity of the airways are based on a comparison of images or maps of the plurality of tubes and images or maps of the airways, the images or maps generated from the raw image data
wherein the plurality of tubes are arranged in a two-dimensional grid, wherein:
lumen size of the plurality of tubes increases along one of the axis of the grid, and
along the other axis of the grid, the lumen size of the tubes remains fixed while the outer diameter of the tubes increases.

2. The system according to claim 1, wherein the plurality of tubes include a tube for each of a plurality of combinations of lumen size and wall thickness.

3. The system according to claim 2, wherein the plurality of combinations of lumen size and wall thickness include lumen sizes spanning from 1-10 millimeters (mms) in 1 mm increments and wall thicknesses spanning from 0.1-5 mms in 0.1 mm increments.

4. The system according to claim 1, wherein the hardware phantom is embedded within the imaging scanner or a patient support of the system, such that the ROI and the hardware phantom are scanned simultaneously.

5. The system according to claim 1, wherein the imaging scanner is a computed tomography (CT) scanner and the plurality of tubes have Hounsfield unit values around the same as airway walls.

6. The system according to claim 1, wherein the processor is further programmed to:
measure lumen sizes and wall thicknesses of the plurality of tubes of the hardware phantom from the raw image data;
generate a lookup table based on the measured lumen sizes and wall thicknesses and known lumen sizes and wall thicknesses of the plurality of tubes; and,
measure the walls of the airways using the raw image data using the lookup table.

7. The system according to claim 1, wherein the processor is further programmed to:
compare the images or maps of the plurality of tubes to the images or maps of the airways to determine correspondances between the plurality of tubes and the airways;
generate the image of the ROI based on the correspondances, wherein at least one of:
opacity of each airway in the image is based on a match quality with a corresponding tube; and,
color of each airway in the image is based on a color code assigned to a corresponding tube.

8. The system according to claim 1, wherein the at least one processor is further programmed to:
display images or maps of the plurality of tubes and images or maps of the airways to allow visual comparison, wherein selection of a tube on the images or maps of the tubes highlights a corresponding airway in the images or maps of the airways, and wherein selection of an airway in the images or maps of the airways highlights a corresponding tube in images or maps of the tubes.

9. The system according to claim 1, wherein the processor is further programmed to:
display the image on a display device, wherein selecting a region of the image displays a corresponding region in another image or map of the ROI.

10. A method for analyzing airways of a patient, said method comprising:
receiving raw image data from an imaging scanner which scans a region of interest (ROI), including the airways, and a hardware phantom, the hardware phantom including a plurality of tubes representative of airways, the plurality of tubes including different lumen sizes and/or wall thicknesses;
correcting measurements of walls of the airways based on measurements of lumen size and/or wall thickness of the plurality of tubes and known lumen size and/or wall thickness of the plurality of tubes, the measurements made from the raw image data; and
generating an image of the ROI in which color and/or opacity of the airways are based on a comparison of images or maps of the plurality of tubes and images or maps of the airways, the images or maps being generated from the raw image data; and
wherein the plurality of tubes are arranged in a two-dimensional grid, wherein:
lumen size of the plurality of tubes increases along one of the axis of the grid, and
along the other axis of the grid, the lumen size of the tubes remains fixed while the outer diameter of the tubes increases.

11. The method according to claim 10, wherein the plurality of tubes include a tube for each of a plurality of combinations of lumen size and wall thickness.

12. The method according to claim 10, wherein the imaging scanner is a computed tomography (CT) scanner and the plurality of tubes have Hounsfield unit values about the same as airway walls.

13. The method according to claim 10, wherein the plurality of tubes are arranged in a two-dimensional grid, wherein lumen size of the plurality of tubes increases from an origin of the grid along one of the axis of the grid and wall thickness increases from the origin along the other axis of the grid.

14. The method according to claim 10, further including:
measuring lumen sizes and wall thicknesses of the plurality of tubes of the hardware phantom from the raw image data;
generating a lookup table based on the measured lumen sizes and wall thicknesses and known lumen sizes and wall thicknesses of the plurality of tubes; and,
measuring the walls of the airways using the raw image data using the lookup table.

15. The method according to claim 10, further including:
comparing the images or maps of the plurality of tubes to the images or maps of the airways to determine correspondances between the plurality of tubes and the airways;
generating the image of the ROI based on the correspondances, wherein at least one of:
opacity of each airway in the image is based on a match quality with a corresponding tube; and,
color of each airway in the image is based on a color code assigned to a corresponding tube.

16. A non-transitory computer readable medium carrying software which controls one or more processors to perform the method according to claim 10.

17. A hardware phantom for diagnostic imaging, said hardware phantom comprising:
a plurality of tubes representative of typical airway sizes and arranged in a two-dimensional grid, wherein:
a lumen size of the plurality of tubes increases along one of the axis of the grid, and
along the other axis of the grid, the lumen size of the tubes remains fixed while the outer diameter of the tubes increases whereby wall thickness increases.

18. The hardware phantom according to claim 17, in combination with a computer readable medium carrying software which controls one or more processors to:
receive raw image data from an imaging scanner which scans a region of interest (ROI) of a patient, including airways, and the hardware phantom;
at least one of:
correct measurements of walls of the airways based on measurements of lumen size and/or wall thickness of the plurality of tubes and known lumen size and/or wall thickness of the plurality of tubes, the measurements made from the raw image data; and,
generate an image of the ROI in which color and/or opacity of the airways are based on a comparison of images or maps of the plurality of tubes and images or maps of the airways, the images or maps being generated from the raw image data.

19. A computed tomography (CT) system comprising:
the hardware phantom according to claim 17; and,
a CT scanner having a patient support which supports the hardware phantom and a patient to be imaged to scan the hardware phantom in conjunction with the patient to create raw image data.

* * * * *